United States Patent [19]

Fujieda

[11] Patent Number: 5,565,939
[45] Date of Patent: Oct. 15, 1996

[54] WIRELESS OPHTHALMIC APPARATUS

[75] Inventor: Masanao Fujieda, Toyohashi, Japan

[73] Assignee: Nidek Co., Ltd., Japan

[21] Appl. No.: 398,121

[22] Filed: Mar. 3, 1995

[30] Foreign Application Priority Data

Mar. 31, 1994 [JP] Japan ................................. 6-087592

[51] Int. Cl.⁶ ....................................................... A61B 3/10
[52] U.S. Cl. .......................... 351/212; 351/205; 351/211; 351/247
[58] Field of Search .................................... 351/200, 205, 351/212, 211, 221, 247, 246, 218, 217, 216, 215

[56] References Cited

FOREIGN PATENT DOCUMENTS 349228A  1/1990  European Pat. Off. ................ 351/200

5-154103  6/1993  Japan .

*Primary Examiner*—William L. Sikes
*Assistant Examiner*—Hung Xuan Dang
*Attorney, Agent, or Firm*—Rossi & Associates

[57] ABSTRACT

An ophthalmic apparatus comprises a first ophthalmic device and a second ophthalmic device. The first ophthalmic device is provided with a first examining part for examining optical characteristics of examinee's eye, a first memory device for memorizing data detected by the first examining part, and device for transmitting by wireless the detected data of the first memory device to the second ophthalmic device. The second ophthalmic device is provided with a second examining part for examining optical characteristics of examinee's eye, device for receiving the detected data of the first ophthalmic device transmitted by the wireless transmitting device, a second memory device for memorizing data detected by the second examining part, and device for outputting the detected data of the first and the second examining parts respectively in a predetermined format.

13 Claims, 2 Drawing Sheets

WIRELESS OPHTHALMIC APPARATUS

BACKGROUND OF THE INVENTION

1. Field of the Invention

The present invention relates to an ophthalmic apparatus for examining optical characteristics of examinee's eye, and more particularly to output of measured results by a compact ophthalmic apparatus typified by hand held typed apparatus to the outside.

2. Description of Related Art

Conventionally, known are ophthalmic apparatuses such as an eye refracting power measurement device, a radius of curvature measurement device and a tonometer etc. These apparatuses are generally constructed as a single equipment respectively and used as installed on a dedicated table. Each of apparatuses is provided with a printer and an interface dedicated for memory and output for instance of the measured data.

With the advance of electronics, apparatuses of hand-held type, a tonometer and others have been proposed recently. This apparatus of hand-held type is provided with a printer unit dedicated for outputting measured data, wherein the printer unit is connected to the measuring unit with a cable.

However, when a cable connects the measuring unit and the printer unit in such a way, the existence of the cable obstructs movement of the apparatus and so on, reducing merits of the hand held type apparatus, that the apparatus is easy to move and capable of conducting examination according to the condition of an examinee. If a printer unit is provided in a hand-held part of the apparatus it spoils an advantage of the hand-held type in that the apparatus' lightness facilitates its operation.

SUMMARY OF THE INVENTION

The present invention has been made in view of the above circumstances and has an object to overcome the above problems and to provide an ophthalmic apparatus having an output system capable of providing the similar function as conventional apparatuses of fixed type in even apparatuses of hand-held type without spoiling its characteristic merits.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention comprises a first ophthalmic device and a second ophthalmic device, the first device comprising a first examining part for examining optical characteristics of examinee's eye, a first memory means for memorizing data detected by the first examining part, and means for transmitting by wireless the detected data of the first memory means to the second ophthalmic device, the second ophthalmic device comprising a second examining part for examining optical characteristics of examinee's eye, means for receiving the detected data of the first ophthalmic device transmitted by the wireless transmitting means, a second memory means for memorizing data detected by the second examining part, and means for outputting the detected data of the first and the second examining parts respectively in a predetermined format.

According to the present invention, even if one ophthalmic apparatus is not provided with devices for outputting data to the outside, such as a special purpose printer and the like, it can use outputting function provided in another ophthalmic apparatus in common by use of data communication between these ophthalmic apparatuses. Accordingly, the space for the apparatus may be reduced because of unnecessary of an individual dedicated printer unit.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

Figure 1:
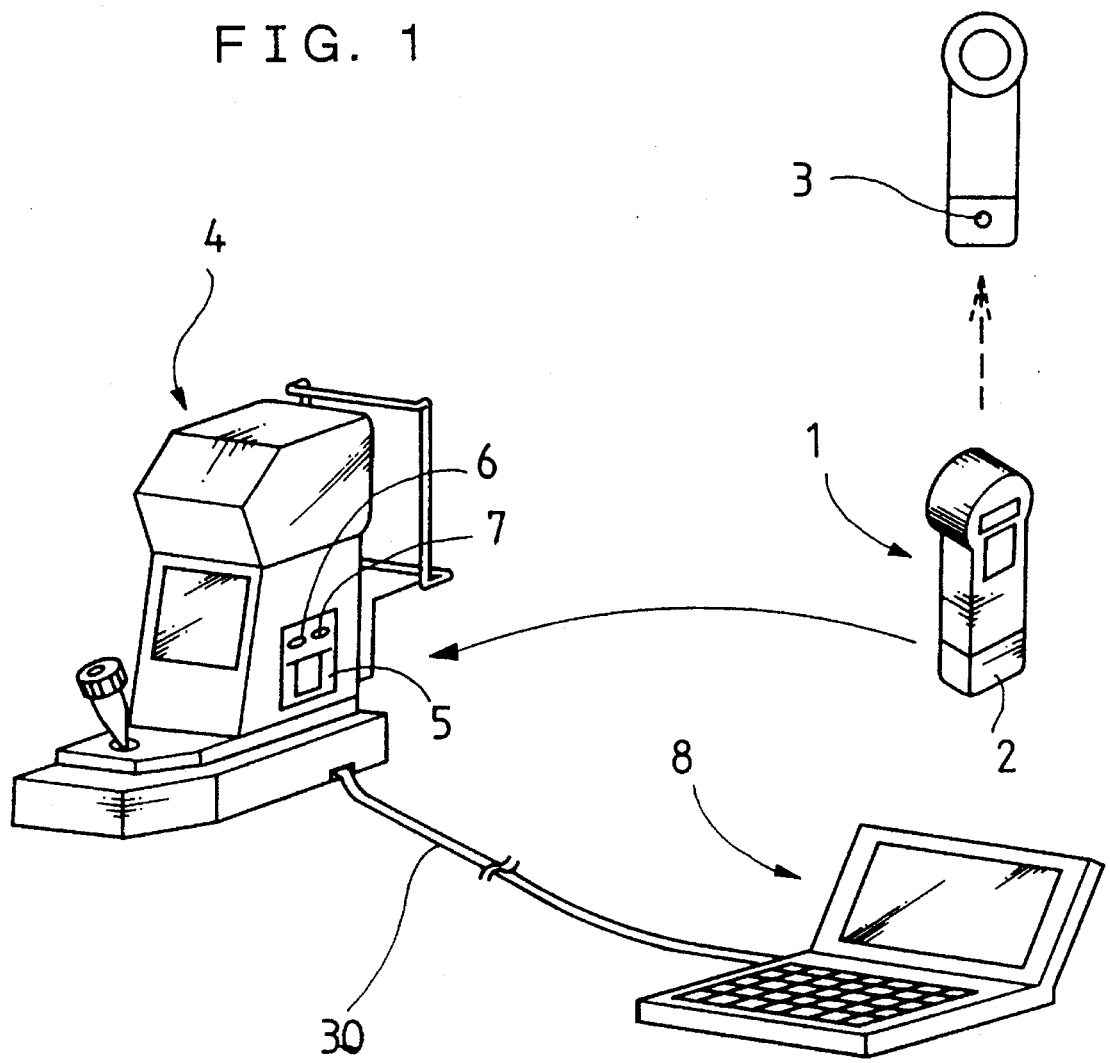
FIG. 1 is a schematic view of a construction of the apparatus of an embodiment in accordance with the present invention.

A detailed description of one preferred embodiment of an ophthalmic apparatus embodying the present invention will now be given referring to the accompanying drawings. FIG. 1 shows a system construction of the apparatus in the present embodiment, mainly including a cornea shape measurement device 1, a non-contact tonometer 4 and a computer 8.

The cornea shape measurement device 1 is of hand-held type and driven by a battery 2 provided in the device 1, thereby to be suitable for the operation as held in examiner's hand. The applicant of the present patent application proposed previously a cornea shape measuring apparatus which has a printer as a separated unit and is driven by battery in Japanese Patent Application No. 5-154420 (Title of the invention: An ophthalmic apparatus) which corresponds to U.S. patent application Ser. No. 08/142,941. The optical system of the previous proposed apparatus is used also in the present embodiment, wherein the optical system projects light of index to examinee's eye and the shape of the cornea is calculated based on deflection reflected from the cornea. Accordingly, the detail explanation of the optical system is not repeatedly described herein.

The cornea shape measuring device 1 is provided with an emitting window 3 for data transfer by optical communication.

The non-contact tonometer 4 is of fixed type and provided on its side surface with a printer 5 for printing out measured data, a light receiving window 6 for receiving optical communication from the cornea shape measuring device 1 and an indicator 7 for informing an examiner of completion of receiving. The construction itself of the measuring system of the non-contact tonometer 4 has no relevance to the present invention, a description thereof is omitted herein.

Numeral 8 is a computer for data acquisition and control, which is connected with the non-contact tonometer 4 with a cable 30.

Figure 2:
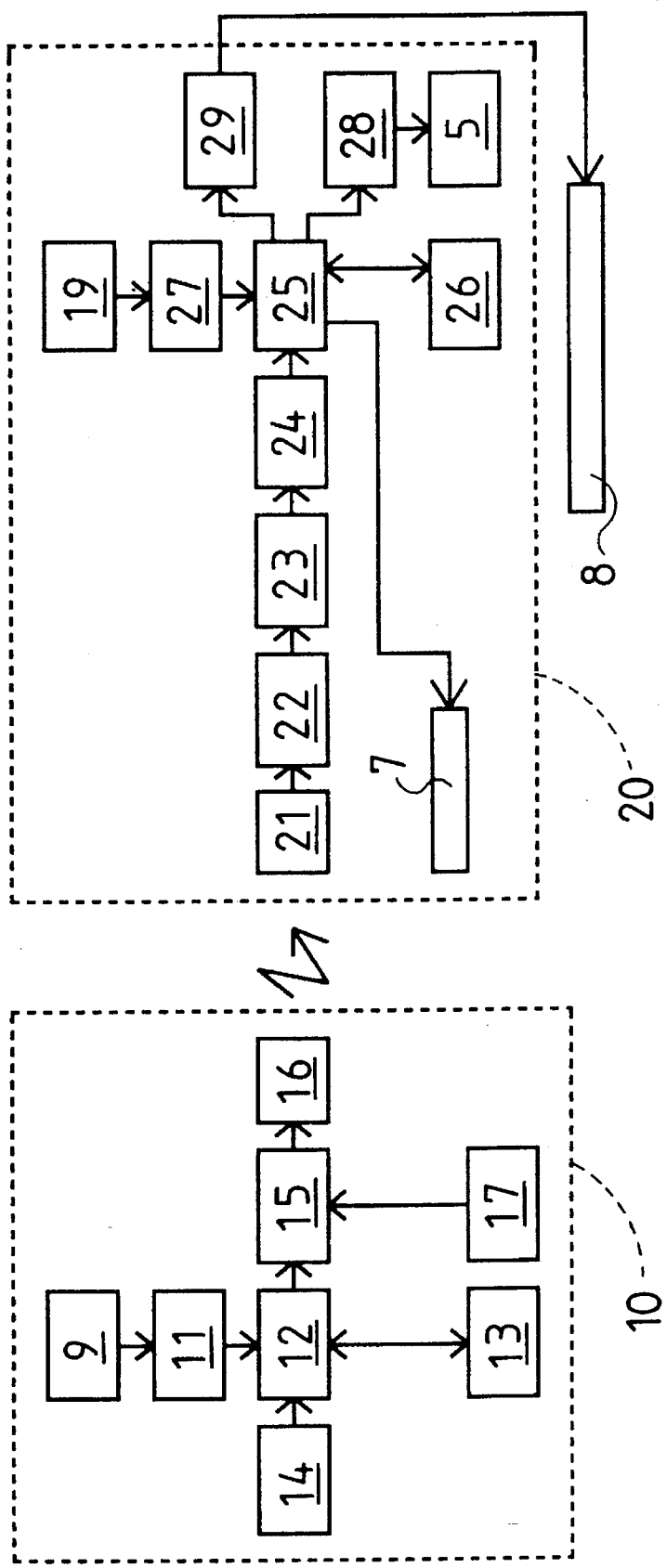
FIG. 2 is a block diagram Of main electric systems to optically communicate measured data of an cornea shape measuring apparatus 1 to a non-contact tonometer 4 in the embodiment.

FIG. 2 is a block diagram of main electric systems for transmitting measured data from the cornea shape measuring device 1 to the non-contact tonometer 4 by optical communication.

Numeral 10 is a block diagram of an electric system of the cornea shape measuring device 1, wherein a detecting signal from a measuring part 9 is processed through a predetermined process in a measurement processing circuit 11 and input to a microcomputer circuit 12. Microcomputer circuit 12 processes then the detecting signal to acquisition measured data, and stores the data in a memory 13.

In this electric system, when a print switch 14 is depressed, the microcomputer circuit 12 reads out the measured data stored in the memory 13, expands the measured data to printing format for print out, and converts the data into a serial signal. It is also possible to expand the measured data to the printing format in the electric system of the non-contact tonometer alternatively. The microcomputer 12 drives a driver circuit 15 to emit a light emitting element 16, thereby to transmit the measured data converted into serial signal as optical pulse signal.

Optical communication by the light emitting element 16 is transmitted with the carrier wave of carrier frequency which a carrier clock 17 generates and the serial signal of the measured data both which are superposed on in the driver circuit 15 in order to prevent the influence of outer disturbed light from exercising thereon. To conduct transmission with the apparatus held in examiner's hand, it is preferable to transfer of all measured data within one or two seconds. Accordingly, to correspond to high-speed data transfer rate being 9,800–19,200/bps, the carrier frequency generated by the carrier clock 17 is determined to be about 200–500 KHz which is 10 times or more than the data transfer rate.

Numeral 20 is a block diagram of an electric system of the non-contact tonometer 4.

In the electric system, numeral 21 is a light receiving element having wide directivity and serves for receiving the optical communication from the cornea shape measuring device 1. The optical signal of the measured data received by the light receiving element 21 is converted into voltage, amplified, and then transmitted to a band pass filter 22.

The band pass filter 22 is for transmitting only the serial signal having a carrier frequency described above and removing noise signals of outer disturbed light of a fluorescent light and the like. Signal passed through the band pass filter 22 is transmitted to a carrier removing circuit 23 to remove the carrier wave, so that signal components which have been superposed on the carrier wave are fetched accordingly. The signal is processed in a waveform shaping circuit 24 so as to have a waveform and input to a microcomputer circuit 25.

Numeral 26 is a memory having two regions, one for memorizing measured data transmitted from a measuring part 19 of the non-contact tonometer 4 and processed via a measurement processing circuit 27 and another for memorizing data received from the outer device, which is the cornea shape measuring device 1 in the present embodiment. These data are separately stored in individual regions of the memory 26 by control of the microcomputer circuit 25.

Numeral 28 is a printer circuit connected to the printer 5 and numeral 29 is a serial communication circuit connected to the computer 8 which is an outer device.

In the apparatus constructed as described above, operation to output measured data of the cornea shape measuring device 1 to the outside, by printing out and the like will be described hereinafter.

While operating the cornea shape measuring device 1 in one hand, the examiner measures the radius of curvature of examinee's cornea with the device 1. Signal on the cornea measured by the measuring part 9 of the device 1 is processed in the microcomputer 12 via the measurement processing circuit 11 and stored in the memory 13 as measured data.

After completion of the measurement, when the examiner holds the device 1 so as to aim the emitting window 3 to the light receiving window 6 of the non-contact tonometer 4 and depresses the print switch 14, the microcomputer circuit 12 accesses the measured data from the memory 13, drives the driver circuit 15 to emit the light emitting element 16, and thereby transmits the measured data toward the non-contact tonometer 4.

When the light receiving element 21 of the non-contact tonometer 4 detects optical signal, the signal of the measured data is input to the microcomputer circuit 25 via the band pass filter 22, the carrier removing circuit 23 and the waveform shaping circuit 24. Signals of the measured data successively input to the microcomputer circuit 25 in turn stored in the outer data storing region of the memory 26 until the signal indicating completion of all data transfer is input to the microcomputer circuit 25.

Receiving the completion signal of all data transfer, the microcomputer circuit 25 subsequently checks whether all data have been received properly through a predetermined process. When judging that all data have been properly received, the microcomputer circuit 25 drives the indicator 7 to turn on thereby to indicate it to the examiner. If the indicator 7 does not turn on, then the examiner depresses the print switch 14 again to transmit the measured data. It is possible to add a function to inform the examiner with a buzzer etc. when the non-contact tonometer 4 has not received the data properly.

In such a way, when all data have been received properly, the microcomputer circuit 25 reads out the measured data stored in the region for outer device in the memory 26 and drives the printer circuit 28 to start the printer 5 on printing.

If the printer 5 is printing out the measured data of intraocular pressure at this time, the data transmitted from the outer device being stored in a different memory region from the memory region of apparatus' own in the memory 26, the microcomputer 25 reads out the measured data on the corneal shape from the memory 26 after finishing printing out the measured data on the intraocular pressure, and starts printing of the data.

To conduct data communication by optical communication even while the microcomputer circuit 25 drives the printer circuit 28, it is possible to use an IC (8251 and others) dedicated for serial communication in the microcomputer circuit 25 so as to enable receiving by utilizing interruption signal which is to generate when the receiving buffer of IC is filed with 1 byte data.

If transferring data to the computer 8 connected in the outside of the non-contact tonometer 4, a switch not illustrated is depressed to cause the microcomputer circuit 25 to read out each of the measured data stored in the memory 26 and to transmit to the computer 8 via the serial communication circuit 29. Both transfer of the measured data of the cornea and of the intraocular pressure to the outside computer 8 may be carried out automatically when the microcomputer circuit 25 drives the printer circuit 28.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:

a first ophthalmic device of hand-held type comprising a first examining part for examining optical characteristics of an examinee's eye, a first memory means for memorizing data detected by said first examining part, and wireless transmitting means for transmitting by wireless transmission the detected data memorized in the first memory means; and a second ophthalmic device of fixed type comprising a second examining part for examining optical characteristics of the examinee's eye, receiving means for receiving the detected data of said first ophthalmic device transmitted by said wireless transmitting means, a second memory means for memorizing data detected by said second examining part, and output means for outputting the detected data of the first and the second examining parts in a predetermined format.

2. An ophthalmic apparatus according to claim 1, wherein said output means comprises a printer.

3. An ophthalmic apparatus according to claim 1, wherein said output means comprises communication means for communicating the detected data of the first and second examining parts to a computer.

4. An ophthalmic apparatus according to claim 1, wherein said first ophthalmic device is a cornea shape measuring device and said second ophthalmic device is a non-contact tonometer.

5. An ophthalmic apparatus including an ophthalmic device comprising:

means for examining optical characteristics of an examinee's eye;

memory means for memorizing detected data of said examining means;

output means for outputting the detected data memorized in said memory means;

receiving means for receiving detected data transmitted by wireless transmission from a hand-held ophthalmic device; and control means for controlling said output means so as to output the detected data received at said receiving means from said hand-held ophthalmic device in a predetermined format.

6. An ophthalmic apparatus according to claim 5, wherein said output means comprises a printer.

7. An ophthalmic apparatus according to claim 5, wherein said output means comprises communication means for communicating said detected data memorized in said memory means and said detected data received by said receiving means to a computer.

8. An ophthalmic apparatus according to claim 5, wherein said ophthalmic device is of fixed type.

9. An ophthalmic apparatus according to claim 8, wherein said ophthalmic device is a non-contact tonometer.

10. An ophthalmic apparatus comprising:

a hand-held ophthalmic device including examining means for examining optical characteristics of an examinee's eye, memory means for memorizing detected data of said examining means, wireless transmitting means for transmitting by wireless transmission said detected data memorized in said memory means to a fixed type ophthalmic device;

wherein said fixed type ophthalmic device includes receiving means for receiving the detected data transmitted by the wireless transmitting means and control means for controlling an output means so as to output in a predetermined format the detected data received by said receiving means, wherein the detected data of said examining means of said hand-held ophthalmic device is output through the output means of said fixed type ophthalmic device.

11. An ophthalmic apparatus according to claim 10, wherein said output means comprises a printer.

12. An ophthalmic apparatus according to claim 10, wherein said output means comprises communication means for communicating said detected data to a computer.

13. An ophthalmic apparatus according to claim 10, wherein said hand-held ophthalmic device is a cornea shape measuring device or an eye refracting power measuring device.

* * * * *